US010695338B2

(12) United States Patent
Cardelli et al.

(10) Patent No.: US 10,695,338 B2
(45) Date of Patent: Jun. 30, 2020

(54) CANCER TREATMENT VIA REPOSITIONED TRICYCLIC ANTI-DEPRESSANT-LIKE DRUGS AS ANTI-CANCER AGENTS AND NEW COMBINATIONS OF SUCH DRUGS

(71) Applicant: Board of Supervisors of Louisiana State University and Agricultural and Mechanical College, Baton Rouge, LA (US)

(72) Inventors: James Allen Cardelli, Shreveport, LA (US); Magdalena Liliana Circu, Shreveport, LA (US); Samantha Sarah Dykes, Shreveport, LA (US); Hazem Edmond El-Osta, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 385 days.

(21) Appl. No.: 15/571,917

(22) PCT Filed: May 6, 2016

(86) PCT No.: PCT/US2016/031181
§ 371 (c)(1),
(2) Date: Nov. 6, 2017

(87) PCT Pub. No.: WO2016/179481
PCT Pub. Date: Nov. 10, 2016

(65) Prior Publication Data
US 2018/0133208 A1  May 17, 2018

Related U.S. Application Data

(60) Provisional application No. 62/158,212, filed on May 7, 2015.

(51) Int. Cl.
| A61K 31/46 | (2006.01) |
| A61P 19/02 | (2006.01) |
| A61P 25/00 | (2006.01) |
| A61P 35/00 | (2006.01) |
| A61K 45/06 | (2006.01) |
| A61K 31/4535 | (2006.01) |

(52) U.S. Cl.
CPC .......... *A61K 31/46* (2013.01); *A61K 31/4535* (2013.01); *A61K 45/06* (2013.01); *A61P 19/02* (2018.01); *A61P 25/00* (2018.01); *A61P 35/00* (2018.01)

(58) Field of Classification Search
CPC .... A61K 31/46; A61K 31/4535; A61K 45/06; A61P 19/02; A61P 25/00; A61P 35/00
USPC ........................................................ 514/304
See application file for complete search history.

(56) References Cited

U.S. PATENT DOCUMENTS

| 6,017,760 A | 1/2000 | Jauregui et al. |
| 6,107,043 A | 8/2000 | Jauregui et al. |
| 6,129,911 A | 10/2000 | Faris |
| 6,872,389 B1 | 3/2005 | Faris |
| 2010/0260835 A1 | 10/2010 | Wheeler et al. |
| 2014/0193392 A1 | 7/2014 | Annunziata et al. |

FOREIGN PATENT DOCUMENTS

| WO | WO 03/070249 A1 * | 8/2003 | ........... A61K 31/519 |
| WO | 2014/200705 A1 | 12/2014 | |

OTHER PUBLICATIONS

Funcke et al 'Investigation of 3-(10,11-dihydro-5H-dibenzo[a,d]cycloheten-5-yloxy)tropane citrate (dibenzoheptropine, brontine' Arch. Int. Pharmacodyn., 148(1-2), p. 135-162, 1964.*
English Translation of WO 03/070249 A1.*
El-Osla et al., "A Novel High-Content Screening Approach to Identify Inhibitors of Lysosome Anterograde Trafficking and Tumor Invasion", Proceedings of the AACR Special Conference on Tumor Invasion and Metastasis; Jan. 20-23, 2013; San Diego, CA, Philadelphia, PA: AACR; Cancer Res 2013;73 (3 Suppl): Abstract Nr. B5. http:/cancerres.aacrjournals.org/content/7/3/3_Supplement/B5.short, p. 1, In3, 14, 16, 21-22, See International Search.
Fonseca et al., "Structure-Activity Analysis of Niclosamide Reveals Potential Role for Cytoplasmic pH in Control of Mammalian Target of Rapamycin Complex 1 (mTORC1) Signaling", Journal of Biological Chemistry, vol. 287, No. 21, May 18, 2012, p. 17530, Background, See International Search.
Circu et al., "A Novel High Content Imaging-Based Screen Identifies the Anti-Helminthic Niclosamide as an Inhibitor of Lysosome Anterograde Trafficking and Prostate Cancer Cell Invasion", PLOS ONE COI:10.1371/journal.pone.0146931, Jan. 19, 2016, p. 1-24, See International Search.
International Search Report Corresponding to PCT/US2016/031181 dated Aug. 15, 2016.
Written Opinion Corresponding to PCT/US2016/031181 dated Aug. 15, 2016.
Alternative Routes of Drug Administration—Advantages and Disadvantages (Subject Review), American Academy of Pediatrics, vol. 100, No. 1, Jul. 1997, See Spec., p. 15.
Harris et al., "Drug Delivery Via the Mucous Membranes of the Oral Cavity", Journal of Pharmaceutical Sciences, vol. 81, Issue 1, Jan. 1992, pp. 1-10, See Spec., p. 15.

\* cited by examiner

*Primary Examiner* — Yevgeny Valenrod
(74) *Attorney, Agent, or Firm* — Davis & Bujold PLLC; Charles Holoubek

(57) ABSTRACT

Methods and compositions for treating a lysosomal movement associated disease in an animal, in which the position of lysosomes can influence disease progression, comprising administering an effective amount of a first lysosome migration inhibitor or a pharmaceutically acceptable salt, solvate, clathrate, stereoisomer, enantiomer or prodrug thereof.

9 Claims, 14 Drawing Sheets

CANCER TREATMENT VIA REPOSITIONED TRICYCLIC ANTI-DEPRESSANT-LIKE DRUGS AS ANTI-CANCER AGENTS AND NEW COMBINATIONS OF SUCH DRUGS

CROSS REFERENCE TO RELATED APPLICATIONS/PRIORITY

The present invention claims priority to U.S. Provisional Patent Application No. 62/158,212 filed May 7, 2015, which is incorporated by reference into the present disclosure as if fully restated herein. To the extent that there is any conflict between the incorporated material and the present disclosure, the present disclosure will control.

FIELD OF THE INVENTION

This invention relates generally to the pharmaceutical treatment of cancer and other lysosomal position influenced diseases.

BACKGROUND

Metastatic cancer accounts for 90% of cancer related deaths and no long term successful therapeutic intervention has been discovered. Tumor invasion is one of the key processes that occur leading to metastatic disease, therefore, novel therapeutic approaches are critically needed to slow tumor invasion and slow the formation of metastatic disease. This is especially critical for brain cancer where tumor invasion is the primary reason that patients succumb. Overall, tumor invasion and subsequent metastatic spread of tumor cells is the number one reason why patients with advanced cancer die. Unfortunately, little in the way of clinically beneficial treatments is available to stop the spread of cancer and subsequent formation of metastatic lesions.

Lysosomes are intracellular organelles normally maintaining an acidic pH that are filled with a variety of degradative enzymes including proteases. Historically, lysosomes were thought to be function as the garbage disposal of the cell to help remove internalized cell surface receptors, internalized bacteria and intracellular organelles that had become non-functional.

SUMMARY

Wherefore, it is an object of the present invention to overcome the above mentioned shortcomings and drawbacks associated with the prior art.

The inventors present below data supporting an important role for lysosomal intracellular positioning in tumor invasion, and disclose organelle trafficking as a novel anti-cancer target. The present invention used a novel high content imaging screening method to discover compounds that altered the position of intracellular lysosomes. These compounds block outward movement of tumor cells in response to environmental triggers which normally results in an increase in tumor invasion. Development of drugs towards commercialization, especially those that are repurposed, that target lysosome trafficking could rapidly translate into clinical trials to test their efficacy in slowing tumor invasion and metastasis.

The inventors have observed that lysosomes can "move" or traffic to the cell surface in response to environmental clues to perform a variety of functions, including repair of the plasma membrane, T-cell mediated killing of antigen expressing cells, secretion of proteases and regulation of intracellular signaling pathways to name a few.

The inventors have further observed that the position of lysosomes in tumor cells can profoundly influence protease secretion, tumor growth and invasion. Furthermore, outward movement is triggered by factors in the tumor microenvironment such as extracellular acid pH and growth factors that are known to stimulate tumor invasion and to be poor prognostic indicators for cancer progression.

Outward movement of lysosomes in tumor cells results in increased invasion and protease secretion. The inventors observed that this is not simply a correlation between position of lysosomes and the resultant increase in invasion but in fact the position of lysosome determines invasive potential. Cells with lysosomes that accumulate near the nucleus in general are less invasive. In contrast, when lysosomes move to a more peripheral position, protease secretion increases and tumor cells become more invasive.

Therefore, the inventors predicted that implementation of a high throughput imaging method to locate lysosome proximity to the nucleus would be important tool to help discover drugs that alter lysosome traffic, lower tumor invasion and slow the progression of cancer. The inventors performed a screen using four reposition and phytochemical drug libraries, containing two thousand fifty (2250) compounds. Eighteen drugs were discovered to inhibit outward lysosome movement, at least two of which have not been characterized or used as anti-cancer pharmaceuticals.

a method for treating a lysosomal movement associated disease in an animal, in which the position of lysosomes can influence disease progression, comprising administering an effective amount of a first lysosome migration inhibitor or a pharmaceutically acceptable salt, solvate, clathrate, stereoisomer, enantiomer or prodrug thereof. Alternative embodiments include wherein the lysosomal movement associated disease is one of cancer, arthritis, and a neurological disorder. Alternative embodiments include wherein the first lysosome migration inhibitor is one of deptropine, pizotifen, dihydroergocristine, dihydroergotoxine, mefloquine, raloxifene, niclosamide, harmine, isoquercetin, vindesine, vincristine, vinorelbine, paclitaxel, colchicine, podophyllotoxin, mebendazole, albendazole, and fenbendazole, or a pharmaceutically acceptable salt, solvate, clathrate, stereoisomer, enantiomer or prodrug thereof. Alternative embodiments include the step of administering an effective amount of a second lysosome migration inhibitor or a pharmaceutically acceptable salt, solvate, clathrate, stereoisomer, enantiomer or prodrug thereof. Alternative embodiments include wherein the step of administering a further pharmaceutically active agent. Alternative embodiments include wherein the first lysosome migration inhibitor or a pharmaceutically acceptable salt, solvate, clathrate, stereoisomer, enantiomer or prodrug thereof is formulated with a pharmaceutically acceptable excipient. Alternative embodiments include the step of inhibiting an mTOR signaling pathway. Alternative embodiments include wherein the first lysosome migration inhibitor is one of deptropine and pizotifen, or a pharmaceutically acceptable salt, solvate, clathrate, stereoisomer, enantiomer or prodrug thereof. Alternative embodiments include the step of administering an effective amount the other of deptropine and pizotifen, or a pharmaceutically acceptable salt, solvate, clathrate, stereoisomer, enantiomer or prodrug thereof.

The present invention further relates to a pharmaceutical mixture comprising a first lysosome migration inhibitor; or a pharmaceutically acceptable salt, solvate, clathrate, stereoisomer, enantiomer or prodrug thereof; and a first further pharmacologically effective agent. Alternative embodiments include wherein the first lysosome migration inhibitor is one of deptropine, pizotifen, dihydroergocristine, dihydroergotoxine, mefloquine, raloxifene, niclosamide, harmine, isoquercetin, vindesine, vincristine, vinorelbine, paclitaxel, colchicine, podophyllotoxin, mebendazole, albendazole, and fenbendazole, or a pharmaceutically acceptable salt, solvate, clathrate, stereoisomer, enantiomer or prodrug thereof. Alternative embodiments include wherein the first lysosome migration inhibitor is one of deptropine and pizotifen, or a pharmaceutically acceptable salt, solvate, clathrate, stereoisomer, enantiomer or prodrug thereof. Alternative embodiments include wherein the first further pharmacologically effective agent is a second lysosome migration inhibitor, or a pharmaceutically acceptable salt, solvate, clathrate, stereoisomer, enantiomer or prodrug thereof. Alternative embodiments include wherein the first lysosome migration inhibitor is one of deptropine and pizotifen, or a pharmaceutically acceptable salt, solvate, clathrate, stereoisomer, enantiomer or prodrug thereof, and the first further pharmacologically effective agent the other of deptropine and pizotifen, or a pharmaceutically acceptable salt, solvate, clathrate, stereoisomer, enantiomer or prodrug thereof. Alternative embodiments include wherein further comprising a second further pharmacologically effective agent, the second further pharmacologically effective agent being one of a chemotherapeutic agent, a dementia therapeutic agent, an arthritic therapeutic agent, and a further lysosome migration inhibitor, or a pharmaceutically acceptable salt, solvate, clathrate, stereoisomer, enantiomer or prodrug thereof. Alternative embodiments include wherein the first further pharmacologically effective agent is one of troglitazone, niclosamide and cambinol, or a pharmaceutically acceptable salt, solvate, clathrate, stereoisomer, enantiomer or prodrug thereof. Alternative embodiments include wherein the first further pharmacologically effective agent is a chemical that stimulates lysosome membrane permeabilization to increase efficacy. Alternative embodiments include wherein the first further pharmacologically effective agent is one or more are chemotherapeutic agent. Alternative embodiments include wherein the first further pharmacologically effective agent is one or more dementia therapeutic agents. Alternative embodiments include wherein the first further pharmacologically effective agent is one or more arthritic therapeutic agents.

In a first aspect, the invention features a method for treating or preventing a condition that benefits from inhibition of outward movement of lysosomes from the nucleus in cells in a mammal, where the method includes the administration of an effective amount of a lysosome migration inhibitor, or a pharmaceutically acceptable salt, solvate, or prodrug thereof.

In some embodiments, the lysosome migration inhibitor, or a pharmaceutically acceptable salt, solvate, or prodrug thereof, is administered as a pharmaceutical composition that further includes a pharmaceutically acceptable excipient.

In some embodiments, the mammal is a human.

In other embodiments, the lysosome migration inhibitor is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more therapeutic agents for the treatment or prevention of a cell proliferative disorder.

In further embodiments, the cell proliferative disorder is a cancer.

In a second aspect, the invention features a method for decreasing movement of lysosomes to a peripheral location in a cell in a human with a condition of cancer, where the method includes the administration of an effective amount of lysosome migration inhibitor, or a pharmaceutically acceptable salt, solvate, or prodrug thereof.

In some embodiments, the lysosome migration inhibitor, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of lysosome migration inhibitor between 0.05 µM-10 µM (e.g., between 0.05 µM-5 µM).

In some embodiments, the mammal is a human.

In other embodiments, the lysosome migration inhibitor is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more therapeutic agents for the treatment or prevention of a cell proliferation disorder.

As used herein, the term "delayed release" refers to a pharmaceutical preparation, e.g., an orally administered formulation, which passes through the stomach substantially intact and dissolves in the small and/or large intestine (e.g., the colon). In some embodiments, delayed release of the active agent (e.g., one of the lysosome migration inhibitors as described herein) results from the use of an enteric coating of an oral medication (e.g., an oral dosage form). The active agent may also be referred to as the active compound, active ingredient, active material, and/or the active drug substance.

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably refer to a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" refer to pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

By "immediate release" is meant that the agent (e.g., one of the lysosome migration inhibitors), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, represents a composition containing a compound described herein (e.g., a lysosome migration inhibitor, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, means a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, refers to prophylactic treatment or treatment that prevents one or more symptoms or conditions of a disease, disorder, or conditions described herein (e.g., cancer). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, represents compounds which are rapidly transformed in vivo to the parent compound of the above formula. Prodrugs also encompass bioequivalent compounds that, when administered to a human, lead to the in vivo formation of a lysosome migration inhibitor.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, impeding or reversing the progress of, or alleviating either the disease or condition to which the term applies, or one or more symptoms of such disease or condition.

The term "unit dosage forms" refers to physically discrete units suitable as unitary dosages for human subjects and other mammals, each unit containing a predetermined quantity of active material calculated to produce the desired therapeutic effect, in association with any suitable pharmaceutical excipient or excipients.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Pharmaceutical Compositions The methods described herein can also include the administrations of pharmaceutically acceptable compositions that include the lysosome migration inhibitors, or a pharmaceutically acceptable salt, solvate, or prodrug thereof. Pharmaceutical compositions and dosage forms of the invention comprise one or more active ingredients in relative amounts and formulated so that a given pharmaceutical composition or dosage form inhibits cancer cell proliferation or other disease or condition where lysosome position can influence the disease progression. Preferred pharmaceutical compositions and dosage forms comprise a lysosome migration inhibitor or a pharmaceutically acceptable prodrug, salt, solvate, stereoisomer, enantiomer, or clathrate thereof, optionally in combination with one or more additional active agents. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention (e.g. the lysosome migration inhibitors) can be administered alone, combined, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, $21^{st}$ Ed., Gennaro, Ed., Lippencott Williams & Wilkins (2005), a well-known reference text in this field, and in the USP/NF (United States Pharmacopeia and the National Formulary). In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, $6^{th}$ Edition, Rowe et al., Eds., Pharmaceutical Press (2009).

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration.

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings:

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration:

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery:

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences*, 81(1): 1-10, 1992)

Oral transmucosal absorption is generally rapid because of the rich vascular supply to the mucosa and allows for a rapid rise in blood concentrations of the therapeutic ("American Academy of Pediatrics: Alternative Routes of Drug Administration—Advantages and Disadvantages (Subject Review)," *Pediatrics*, 100(1):143-152, 1997).

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimens:

The present methods for treating cancer are carried out by administering one or more lysosome migration inhibitors for a time and in an amount sufficient to result in stabilization and/or reversal of cancer symptoms The amount and frequency of administration of the compositions can vary depending on, for example, what is being administered, the state of the patient, and the manner of administration. The dosage is likely to depend on such variables as the type and extent of progression of the cancer, the severity of the cancer, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of chronic tissue ischemia or slowing its progression.

The amount of I lysosome migration inhibitor per dose can vary. For example, a subject can receive from about 0.1 µg/kg to about 10,000 µg/kg. Generally, the lysosome migration inhibitor is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of lysosome migration inhibitor (e.g., 0.089-3.9 mmol) or 0.1-50 µmol of lysosome migration inhibitor (e.g., 0.1-25 µmol or 0.4-20 µmol).

The frequency of treatment may also vary. The subject can be treated one or more times per day with a lysosome migration inhibitor (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days.

Treatment cycles can be repeated at intervals, for example weekly, bimonthly or monthly, which are separated by periods in which no treatment is given. The treatment can be a single treatment or can last as long as the life span of the subject (e.g., many years).

KITS: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce incidence, duration, and or severity of cancer, cell proliferation disorder, or other diseases associated with lysosome migration.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION

Figure 1:
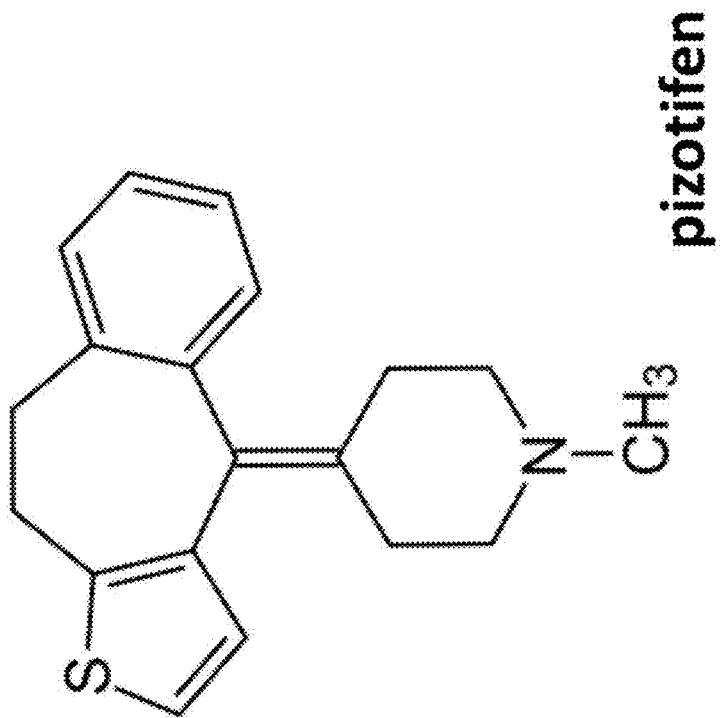
FIG. 1 is a pair of diagrams showing the structures of deptropine and pizotifen.
Figure 1:
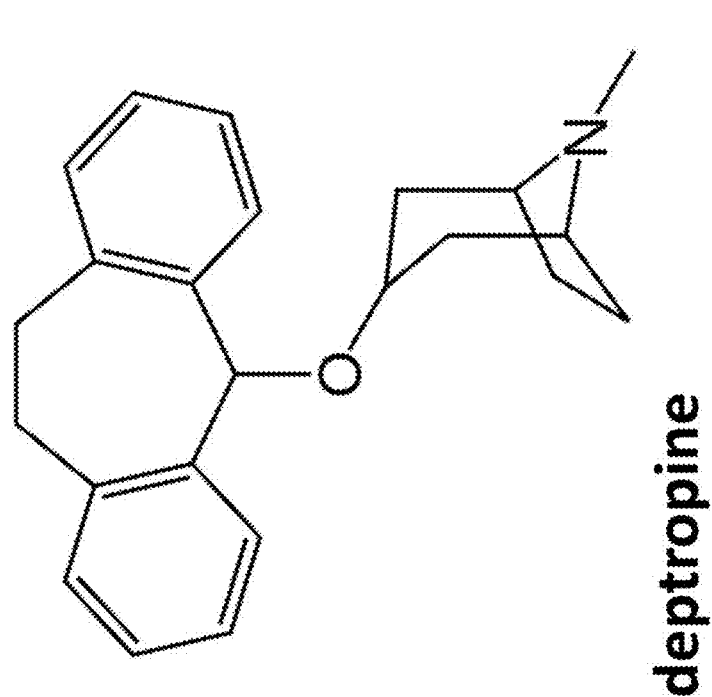

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIG. 1, a brief description concerning the various components of the present invention will now be briefly discussed.

Development of a High Content Imaging-Based Screen:

The followings process was followed to identify chemicals that were lysosome migration inhibitors. DU145 prostate cancer cells were seeded in 96 well flat bottom black walled plates at 4,500 cells per well. All compounds and controls were exposed to RPMI bicarbonate buffered media (pH 6.4). RPMI buffered media titrated at pH of 6.4-6.8 was added to column 12 after the media was removed and serves as negative control (low acidic pH so lysosomes move out). EIPA diluted to a final concentration of 25 uM was added to the wells of column 1 and serves as positive control (lysosomes near the nucleus). The 4 compound libraries chosen to screen were the NIH Clinical Collection (450 drugs), Prestwick (1200 drugs), Prestwick phytochemical and the Green Pharma collection (xx drugs). Compounds were diluted with buffered RPMI media to 2 micrograms per ml concentrations. Individual compounds to be screened were added robotically as a single compound per well through columns 2-11. Plates were incubated at 37 degrees in 5% CO2 for 16 hours then the medium was removed and the cells were fixed with 4% cold paraformaldehyde (Sigma-Aldrich) for 20 minutes at 4 degrees. Fixed cells were washed once with PBS. To stain lysosomes, cells were incubated for 1 hour with LAMP1 antibody (H4A3) diluted in BSP (containing 0.25% BSA and 0.1% saponin in PBS) at 1/200. Cells were then washed with PBS 3 times then incubated for 1 hour with Dylight Donkey anti-mouse diluted at 1/200 in BSP. To stain the nucleus, cells were then washed with PBS 3 times and incubated for 20 minutes with 1×DAPI diluted in PBS. DAPI was washed off with PBS and cells were maintained in PBS for the duration of the screening process. Plates were mounted and read in a Cellomics Arrayscan automated fluorescence imager. The Cellomics platform allows for high content throughput screening by combining fluorescence microscopy with a multi-parameter image analysis. Cells were photographed using 20× objective in 2 fluorescent channels. A total of 15 different fields in each well, and at least 300 cells were imaged per well. The biocompartmental analysis algorithm was used to identify each cell by its nucleus (channel 1 recognized by the DAPI stain) and to generate a cytoplasmic mask (ring) of 12 pixels width in which the inner ring was 6 pixels away from the nucleus. The algorithm calculates the number of lysosomes inside the ring as indicated by fluorescent LAMP-1 positive puncta in channel 2 as a mean ring spot count. Therefore, when lysosomes move away from the nucleus and disperse throughout the cytoplasm, the number of spots representing lysosomes inside the cytoplasmic ring increases (low pH conditions). By contrast, lysosomes cluster near the nucleus the numbers of spot inside the cytoplasmic ring decreases (EIPA treated).

Z'-factor is a simple statistical coefficient used to assess performance and quality of the assay in high-throughput screening. It is calculated with the formula: $Z'=1-(3\sigma ct+3\sigma cb)/|\mu ct-\mu cb|$, where $\mu$ indicates mean, $\sigma$ represents standard deviation, "ct" indicates the positive control, "cb" indicates the negative control. If the Z' factor is small (negative or close to zero), it indicates that the assay conditions have not been optimized or that the assay reaction is not feasible to generate data in this format. If the Z' is more than 0.5, the assay is considered to be high quality assay.

The Z' factor of the assay was determined from the EIPA (positive control) and low pH (negative control). Experiments were run in duplicate. Only plates with positive Z' factor was used for analysis.

A total of 2240 repurposed and natural product drugs were screened for lysosome migration inhibitors and 18 "hits" were identified where the Z' score was at least greater than 50%. There was a hit rate of less than one percent, which supports the specificity of the screen. The 18 chemicals indicated as lysosome migration inhibitors, or chemicals which inhibited lysosomal movement away from the nucleus and inhibited dispersal throughout the cytoplasm, and/or promoted lysosomal clustering near the nucleus.

Nine of the hits belong to a class of drug that disrupts microtubules (Table I below). This is explained by the inventors to because of microtubules playing a major role in movement of lysosomes towards the plasma membrane.

Three of the hits were benzimidazoles (albendazole, fenbendazole and mebendazole) which act as anti-heminthic agents—and are thought to disrupt microtubules in parasites.

Three of the hits were Vinca alkaloids (vindesine, vincristine, and vinorelbine) which are anti-microtubular drugs.

One of the hits was paclitaxel, another microtubular disrupting agent belonging to the taxane class One of the hits was colchicine, another microtubular disrupting agent, used in gout, irritable bowel syndrome and other maladies.

Finally, the ninth member of hits that target microtubules was podophyllotoxin, a non-alkaloid lignin that has been used against HPV induced warts.

Two of the hits were ergot alkaloids, dihydroergocristine mesylate [(5'α,10α)-9,10-Dihydro-12'-hydroxy-2'-(1-methylethyl)-5'-(phenylmethyl)-ergotaman-3',6',18-trione mesylate] and dihydroergotoxine mesylate. These drugs have been used for the treatment of dementia and Alzheimer's.

One of the hits was niclosamide, a beta-phenylbenzamide that uncouples the electron transport chain and is used as an anti-helminthic.

Two of the hits were tricyclic antidepressants (pizotifen malate and deptropine citrate; See FIG. 1) which act as anti-histamines that are used to treat chronic airway obstruction asthma, migraine headaches and treatment of anxiety.

One of the hits was raloxifene, a benzothiophene used as a selective estrogen receptor modulator.

Another hit was mefloquine, a quinolone derivative that is used to treat malaria. [(R*,S*)-2,8-bis(trifluoromethyl)quinolin-4-yl]-(2-piperidyl)methanol Another hit was harmine, a beta-carboline alkaloid used to treat depression.

Another hit was isoquercetin, a flavonoid used in alternative medicine.

A final hit was the compound tetrandrine, a bis-benzylisoquinoline alkaloid and a calcium channel blocker.

Below are chemical structures of a selection of the identified lysosome migration inhibitors:

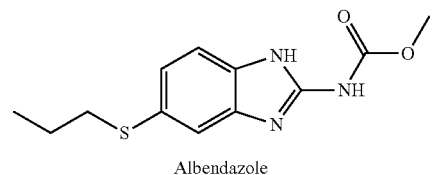

Albendazole

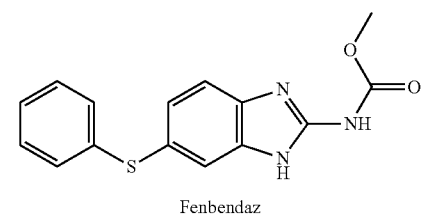
Fenbendaz
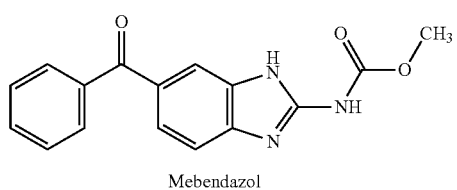
Mebendazol
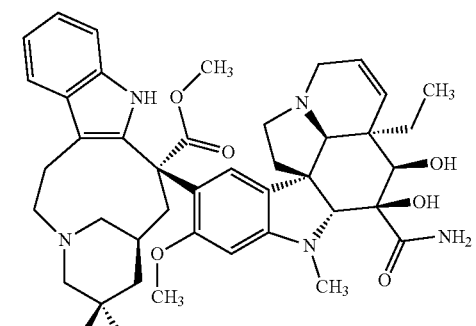
Vindesine
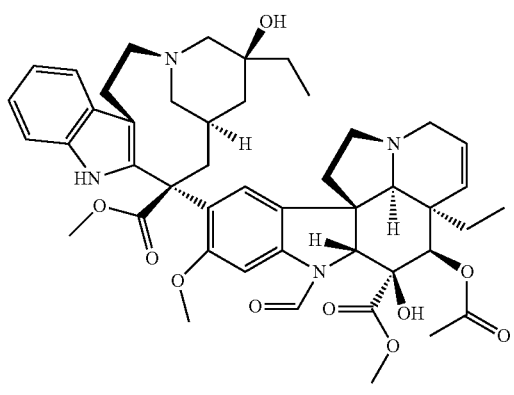
Vincristine
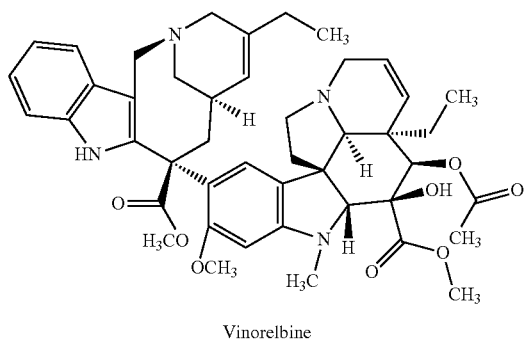
Vinorelbine
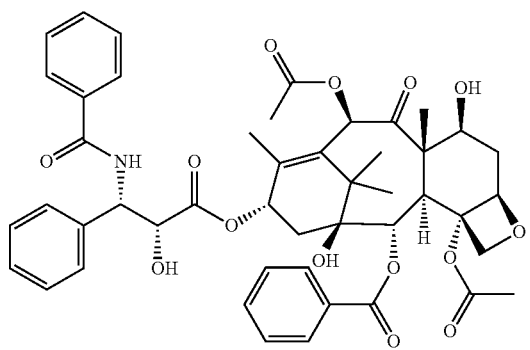
Paclitaxel
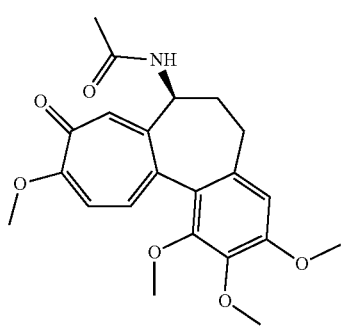
Colchicine
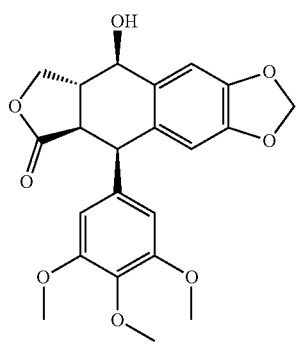
Podophyllotoxin
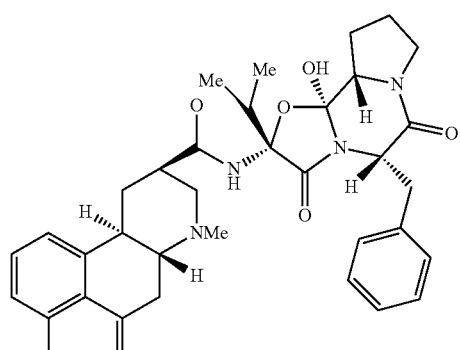
Dihydroergocristine mesylate

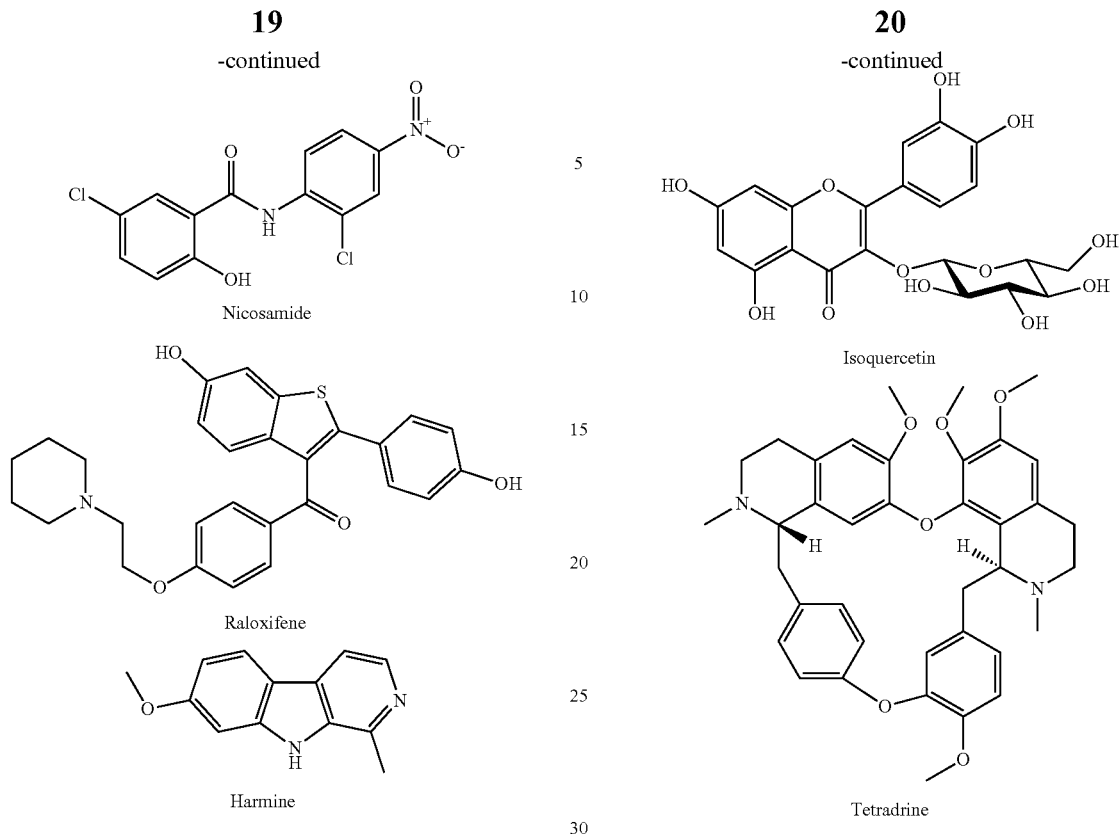

TABLE I

HITS FROM THE CELLOMICS SCREEN (IDENTIFIED LYSOSOME MIGRATION INHIBITORS)

| LIBRARY | PLATE | DRUG | DESCRIPTION |
|---|---|---|---|
| PW | 13F4 | Deptropine citrate | Tricyclic antidepressant -antihistamine and anticholinergic activities. Usage-respiratory tract disorders like chronic airways obstruction, asthma and chronic bronchitis |
| PW | 13D3 | Pizotifen malate | Tricyclic antidepressant -serotonin antagonist also acting as antihistamine with some anticholinergic activity. Usage-recurrent migraine headaches, antidepressant or in the treatment of anxiety or social phobia |
| PWP | 1:E5 | Dihydroergocristine | Ergot alkaloid - a serotonin receptor antagonist and mesylate partial agonism/antagonism of dopaminergic and adrenergic receptors. Usage-cognitive enhancement and treatment of senility and of cerebrovascular insufficiency |
| PWP | 1:E4 | Dihydroergotoxine | Ergot alkaloid-stimulates dopaminergic and mesylate serotonergic receptors and blocks alphaadrenoreceptors. Usage-treatment of dementia and age related cognitive impairments (Alzheimer's) |
| PW | 2E7 | Mefloquine | Quinoline derivative-inhibits heme polymerase Usage - antimalarial agent |
| PW | 11G3 | Raloxifene | Benzothiopheneselective estrogen receptor modulator (SERM). Usage-treatment of osteoporosis |
| PW | 1D11 | Niclosamide | β-Phenylbenzamideuncouples the electron transport chain at ATP synthase. Usage-anti-helminthic; it has activity blocking the migration and invasion of cells overexpressing S100 calcium-binding protein A4 (S100A4) |
| PWP | 1:D5 | Harmine | β-Carboline alkaloid-Monoamine oxidase (MAO) inhibitor. Usage-antidepressant |
| NIH | 3A9 | Isoquercetin | Flavonoid. Usage-alternative medicine |
| NIH | 6A2 | Vindesine | Vinca alkaloidantitubular agent |
| NIH | 6B2 | Vincristine | Vinca alkaloidantitubular agent |
| NIH | 4B4 | Vinorelbine | Vinca alkaloidantitubular |

TABLE I-continued

HITS FROM THE CELLOMICS SCREEN (IDENTIFIED LYSOSOME MIGRATION INHIBITORS)

| LIBRARY | PLATE | DRUG | DESCRIPTION |
|---|---|---|---|
| NIH | 2H6 | Paclitaxel | Taxane- antitubular agent. |
| PW | 5E4 | Colchicine | Colchicum alkaloid-antitubular agent. Usage-gout, irritable bowel syndrome, stomatitis, Behcet's syndrome |
| PW | 10G3 | Podophyllotoxin | Non-alkaloid lignan- antitubular agent. Usage-HPV warts |
| PW | 3F8 | Mebendazole | Benzimidazole- antitubular agent. Usage-antihelminthic |
| PW | 4F8 | Albendazole | Benzimidazole- antitubular agent. Usage-antihelminthic; treatment of giardiasis and of lymphatic filariasis |
| PW | 2E11 | Fenbendazole | Benzimidazole- antitubular agent. Usage-antihelminthic |

From the above identified lysosome migration inhibitors, two representative chemicals were chosen for further validation—deptropine and pizotifen. FIG. 1 illustrates the structures of deptropine and pizotifen, chemicals identified through the high content screen described above as drugs that target lysosome movement and tumor cell invasion. Deptropine ("D") is an anti-cholinergic agent used as an anti-histamine. Deptropine's chemical name is 3a-[(10,11-dihydro-5H-dibenzo[a, d]cyclohepten-5-yl) oxy]1aH,5aH-tropane. Pizotifen ("P") or pizotyline, trade name Sandomigran, is a benzocycloheptene-based drug used as a medicine, primarily as a preventative to reduce the frequency of recurrent migraine headaches. Pizotifen's chemical name is 4-(1-methyl-4-piperidylidine)-9,10-dihydro-4H-benzo-[4,5]cyclohepta[1,2]-thiophene. Both of these drugs share a structure similar to tricyclic antidepressants. These 4 compound libraries had a number of other TCA-like compounds but the other TCA-like compounds were inactive in repositioning lysosomes. Thus, the various TCA-like compounds appear to act with unpredictable high specificity with regard to efficacy in impeding lysosome movement and tumor cell invasion or lack thereof.

Figure 2:
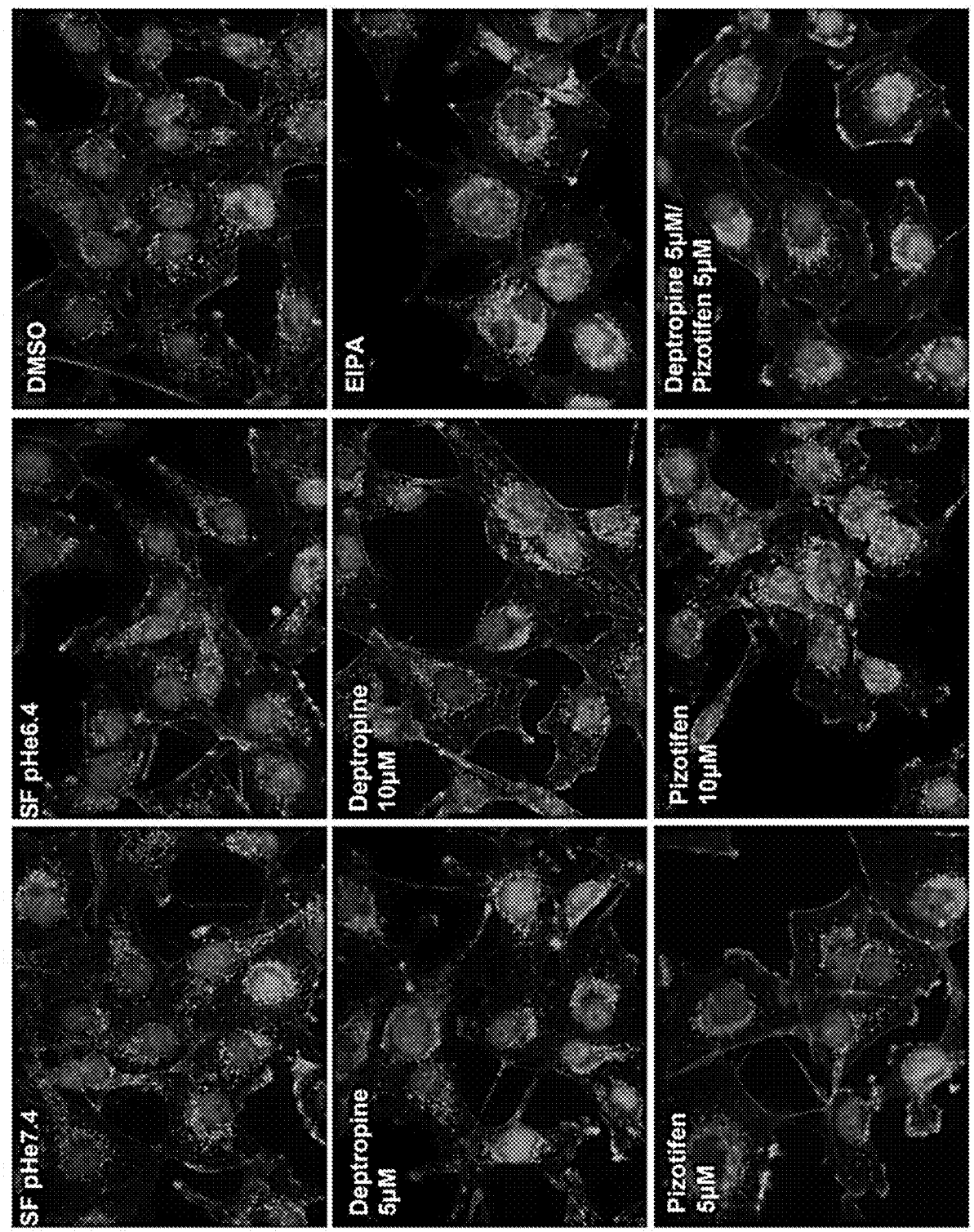
FIG. 2 is nine photographs demonstrating results of treatment with deptropine or pizotifen in A172 glioblastoma cells.

Turning next to FIG. 2, an embodiment is shown that demonstrates the ability of these two drugs block acidic media pH induced lysosome distribution to the peripheral regions of the tumor cell. This figure shows that treatment with deptropine or pizotifen blocks acidic media induced trafficking of lysosomes to the cell periphery in A172 glioblastoma cells. A172 glioblastoma cells were treated overnight with 5 or 10 µM deptropine or pizotifen or with the deptropine or pizotifen in combination at 5 µM concentration. The next day, media was change to low pHe media containing deptropine or pizotifen and the cells were incubated for an additional 2 h. EIPA is a known inhibitor of lysosomal outward movement and represents the positive control. At the end of the incubation time, cells were fixed and stained for LAMP-1, filamentous actin and nuclei. Representative merged IF images depicting the effect of pHe 7.4, pHe 6.4, DMSO or deptropine and pizotifen on the distribution of lysosomes in A172 glioblastoma cells. On color versions of the Figure, red puncta are lysosomes, blue is nuclei and green is actin. As could be seen, lysosomes appear more peripherally distributed in A172 glioma cells than in cells treated with concentrations of 5 to 10 micromolar deptropine or pizotifen. EIPA, a known NHE-1 inhibitor, also prevented lysosome redistribution and induced clustering of lysosomes around the nucleus. Combinations of 5 micromolar of deptropine and pizotifen appear more effective than either drug alone.

Figure 3A:
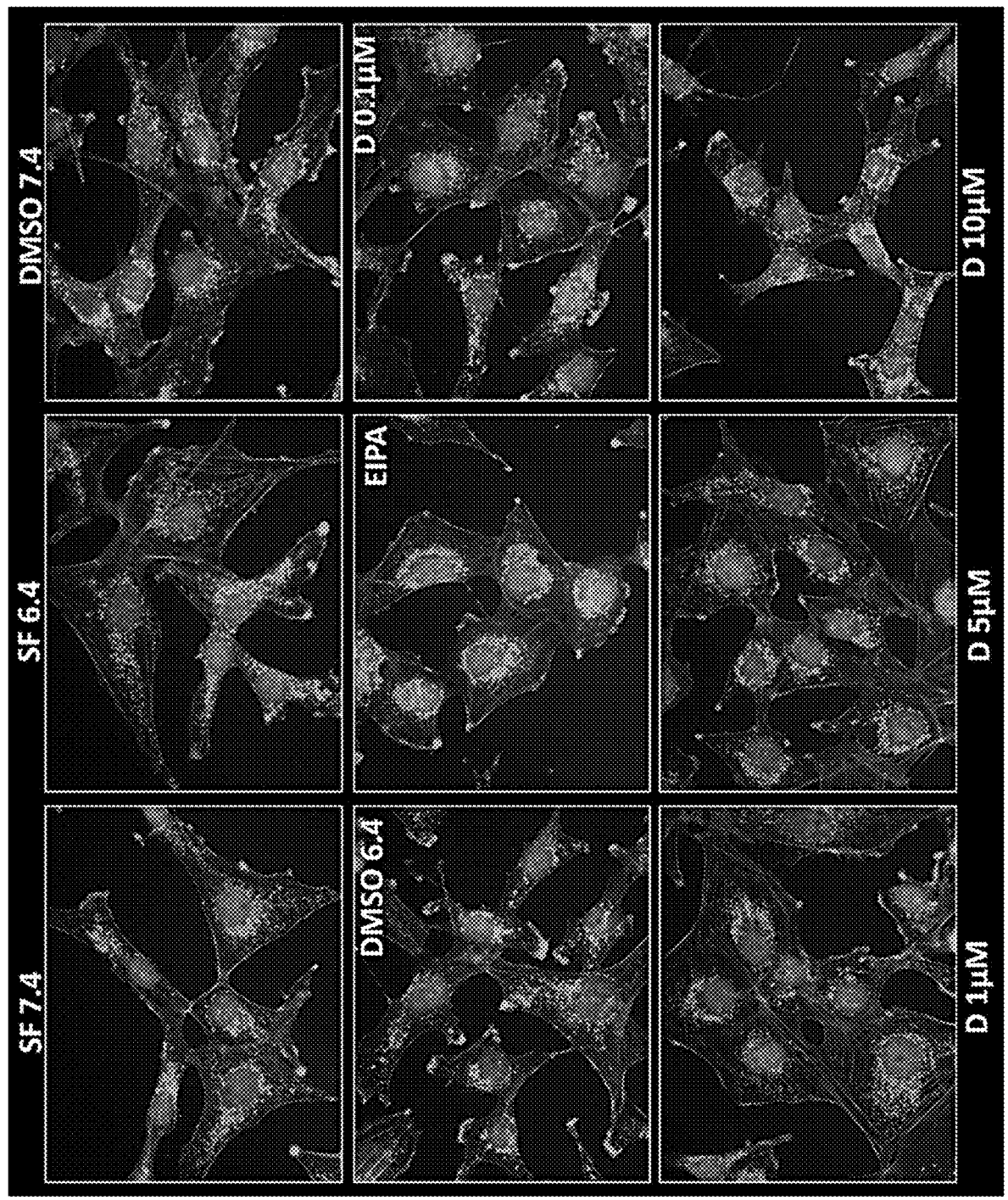
FIGS. 3A-3C show eight or nine photographs each, demonstrating the results of treatment with deptropine in 3A, with pizotifen in 3B, and with combined deptropine and pizotifen in 3C, each in A172 glioblastoma cells.
Figure 3B:
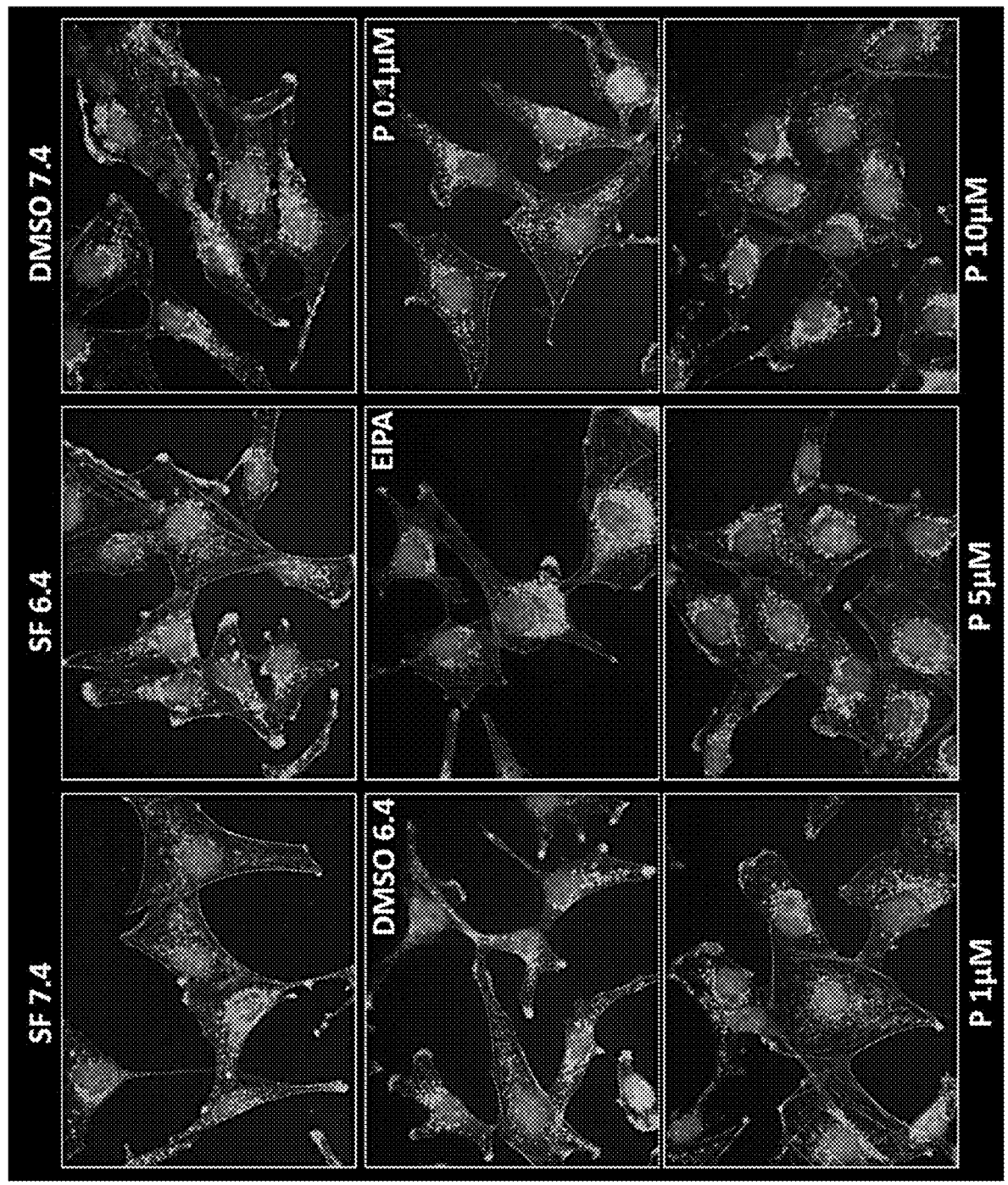
Figure 3C:
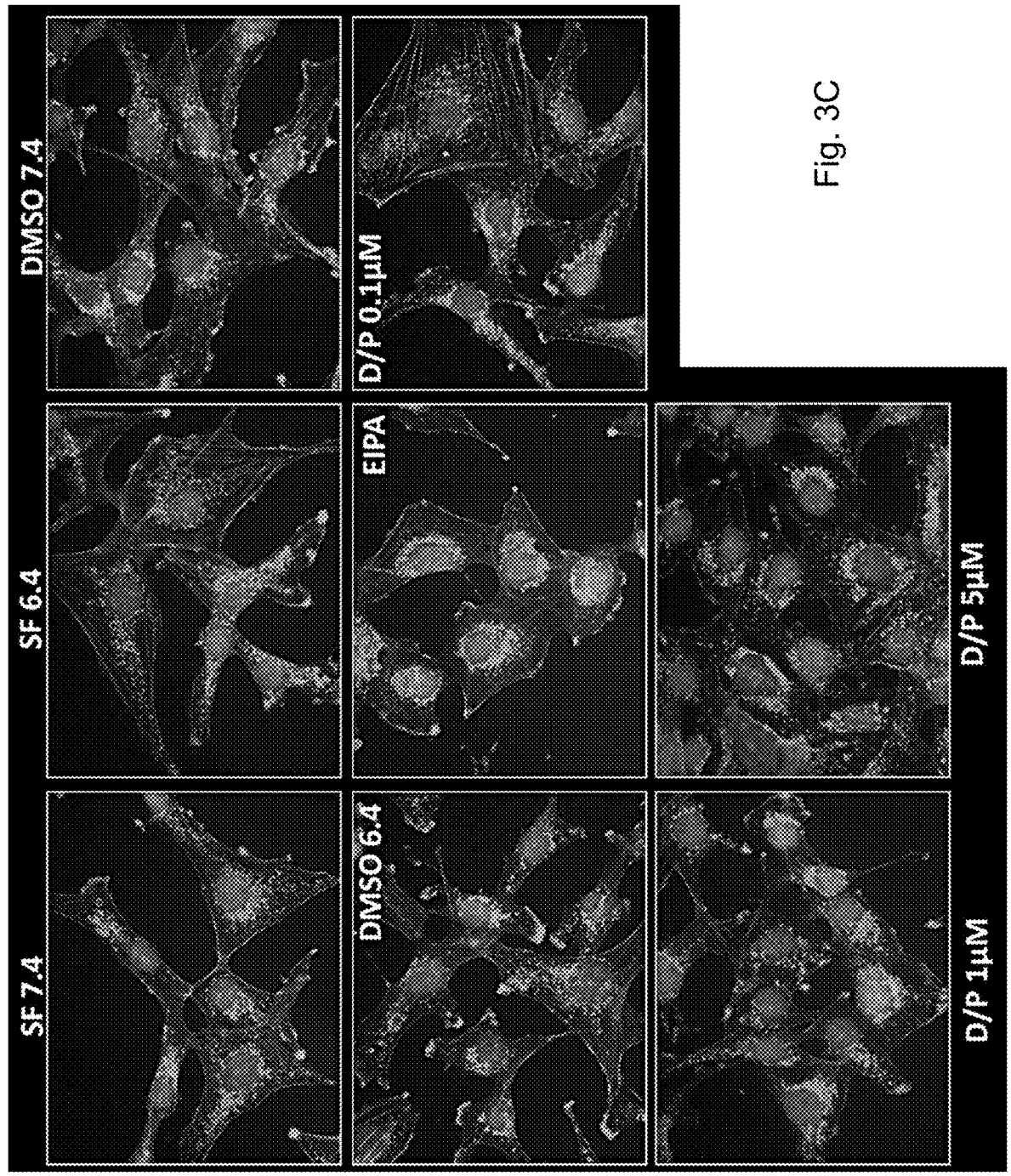

Turning now to FIGS. 3A-3C, a further embodiment demonstrates that deptropine and pizotifen work synergistically, and more effectively at 1 micromolar in combination than at one micromolar alone. Cells were treated as described above with FIG. 2 but included a concentration of 0.1 micromolar and 1 micromolar deptropine and pizotifen. Concentrations of deptropine and pizotifen at one micromolar alone have only a marginal effect on the inward movement of lysosomes, as shown in FIGS. 3A and 3B. However, as shown in FIG. 3C, the combination of both deptropine and pizotifen at one micromolar are effective.

Figure 4:
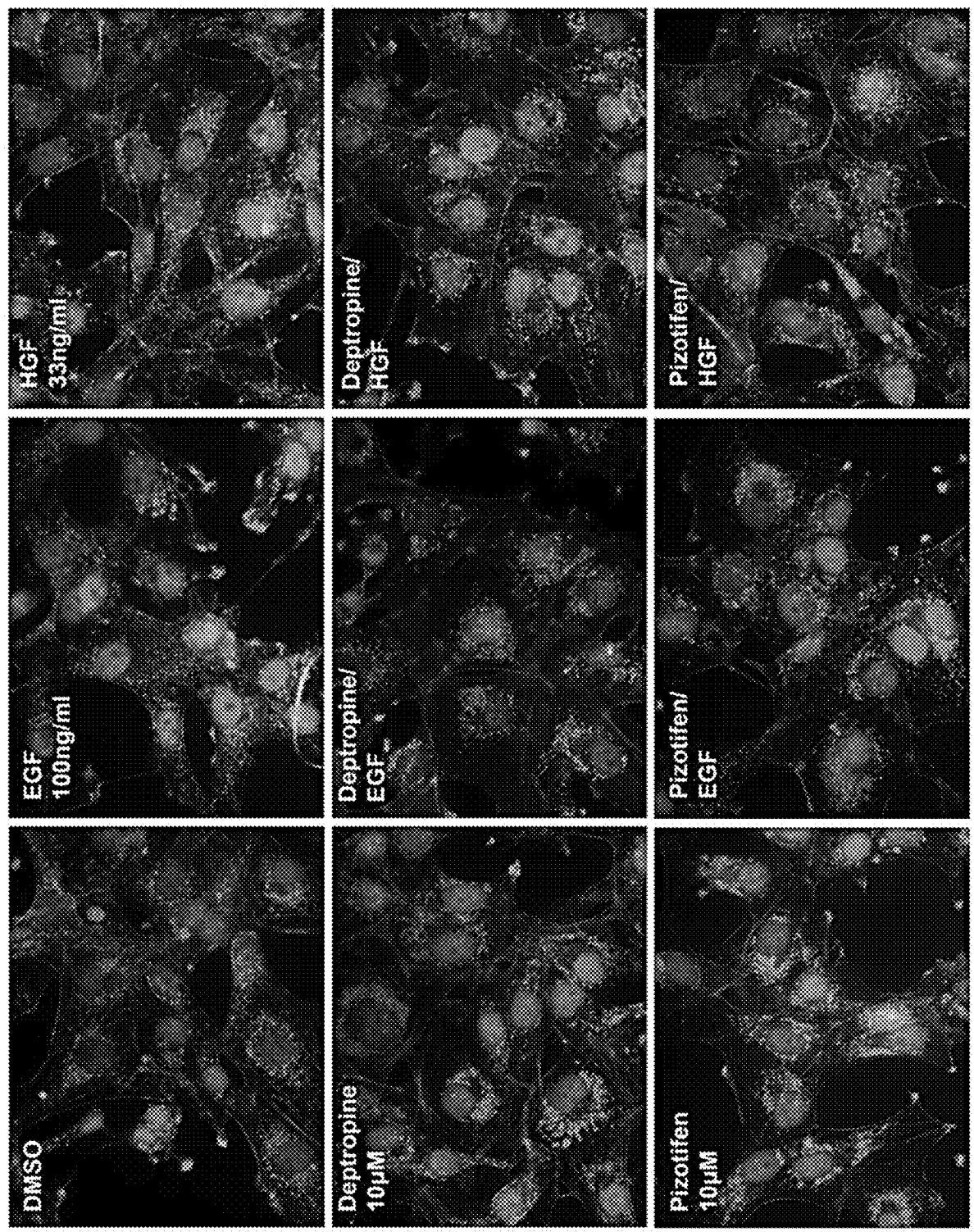
FIG. 4 is nine photographs demonstrating results of treatment with deptropine or pizotifen in A172 glioblastoma cells in the presence or absence of HGF or EGF.

Turning next to FIG. 4, an overnight treatment with deptropine or pizotifen is shown to block trafficking of lysosomes to cell periphery induced by growth factors in A172 glioblastoma cells. In this embodiment deptropine and pizotifen also block lysosome peripheral movement in glioma cells treated with the growth factors HGF and EGF. Both of these growth factors interact with their receptors, c-Met and EGFR, respectively to induce glioma invasion. In this example, A172 glioblastoma cells were treated overnight with 10 µM deptropine or pizotifen in the presence or absence of HGF (33 ng/ml) or EGF (100 ng/ml). At the end of the incubation time, cells were fixed and stained for LAMP-1, filamentous actin, and nuclei. Representative merged IF images depicting the effect of DMSO, 10 µM deptropine or pizotifen and/or HGF, EGF on the distribution of lysosomes (red in color images) in A172 glioblastoma cells. Also shown here are actin (green in color images) and nuclei (blue in color images).

Figure 5:
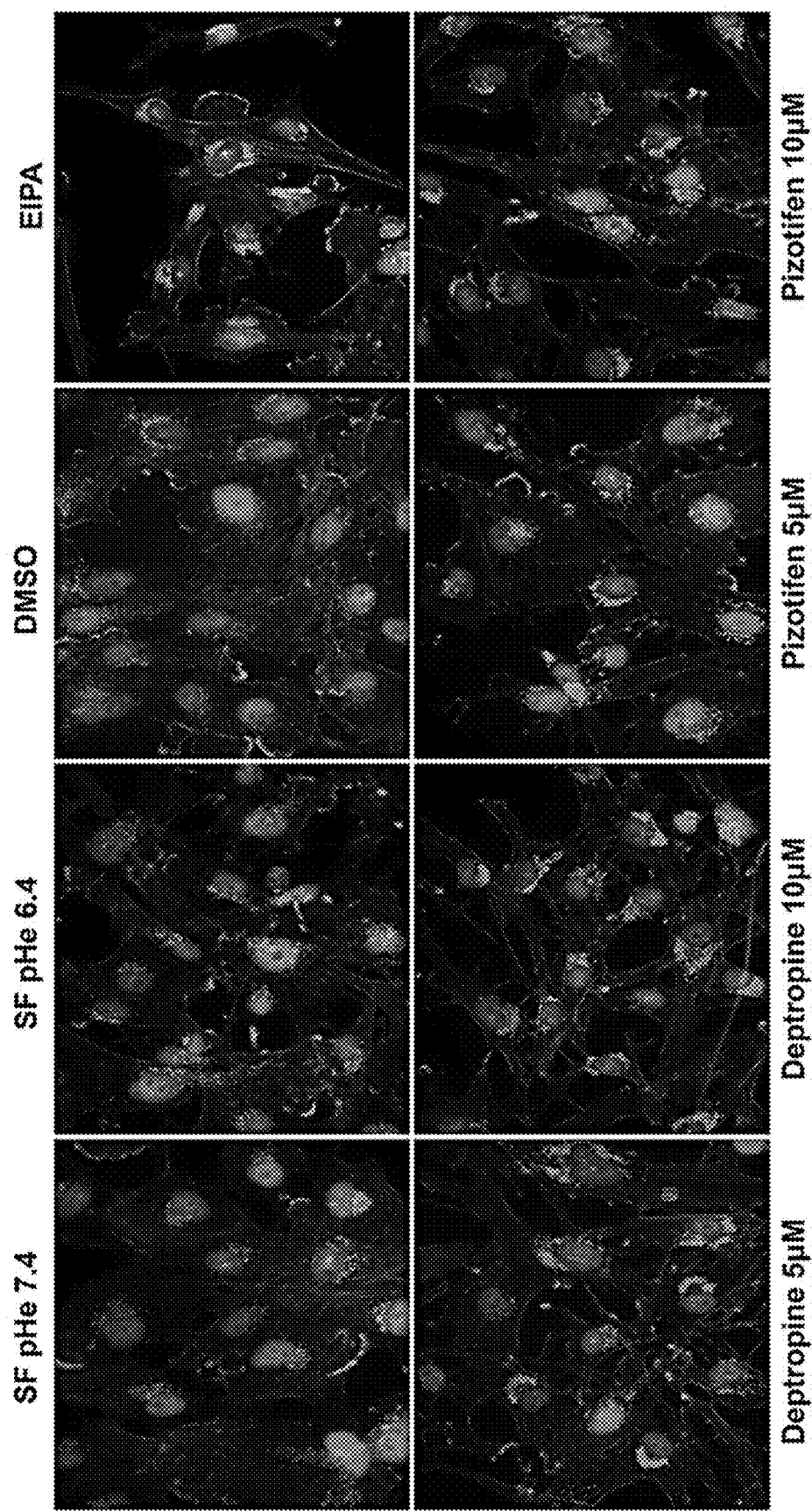
FIG. 5 is eight photographs demonstrating results of treatment with deptropine or pizotifen in U373 glioma cells.

In an additional experiment, following the method whose results are shown in FIG. 2 above but with different cells, the broad range and general effectiveness of deptropine and pizotifen is shown beyond just in A172 glioblastoma cells. Specifically, deptropine and pizotifen were applied to U373 glioma cell lines instead of A172 glioblastoma cells. As shown in FIG. 5, deptropine and pizotifen block lysosome outward movement in U373 cells also.

Figure 6B:
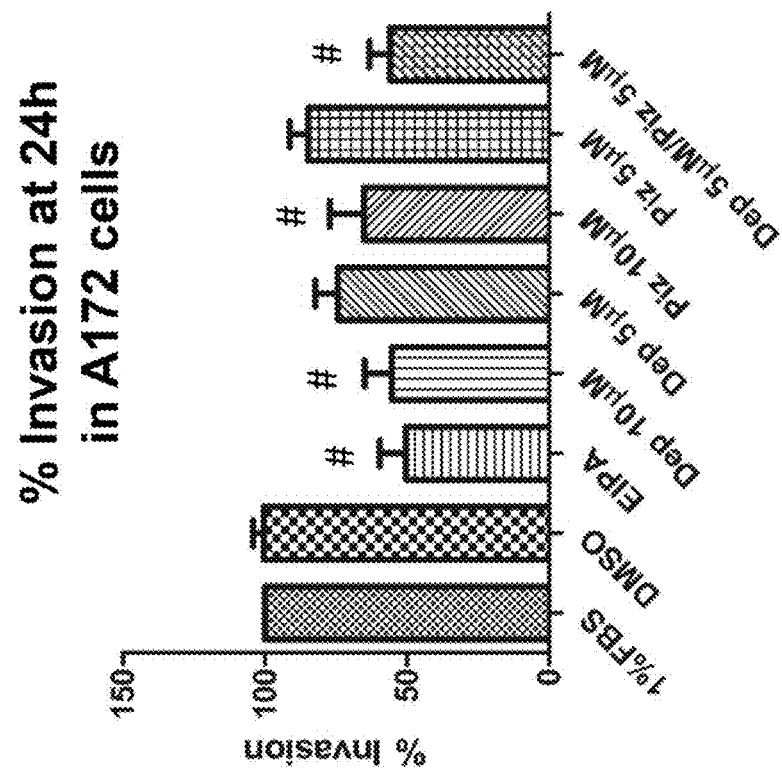
FIGS. 6A and 6B are graphs that display percent migration in FIG. 6A and percent invasion in FIG. 6B through matrigel in A172 glioblastoma cells in the presence various compounds.
Figure 6A:
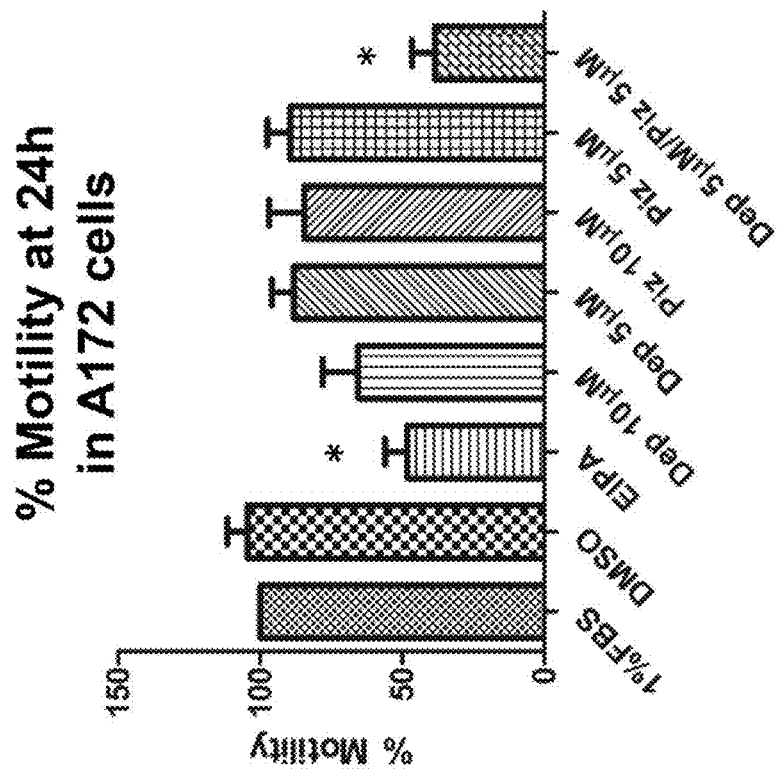
Figure 6C:
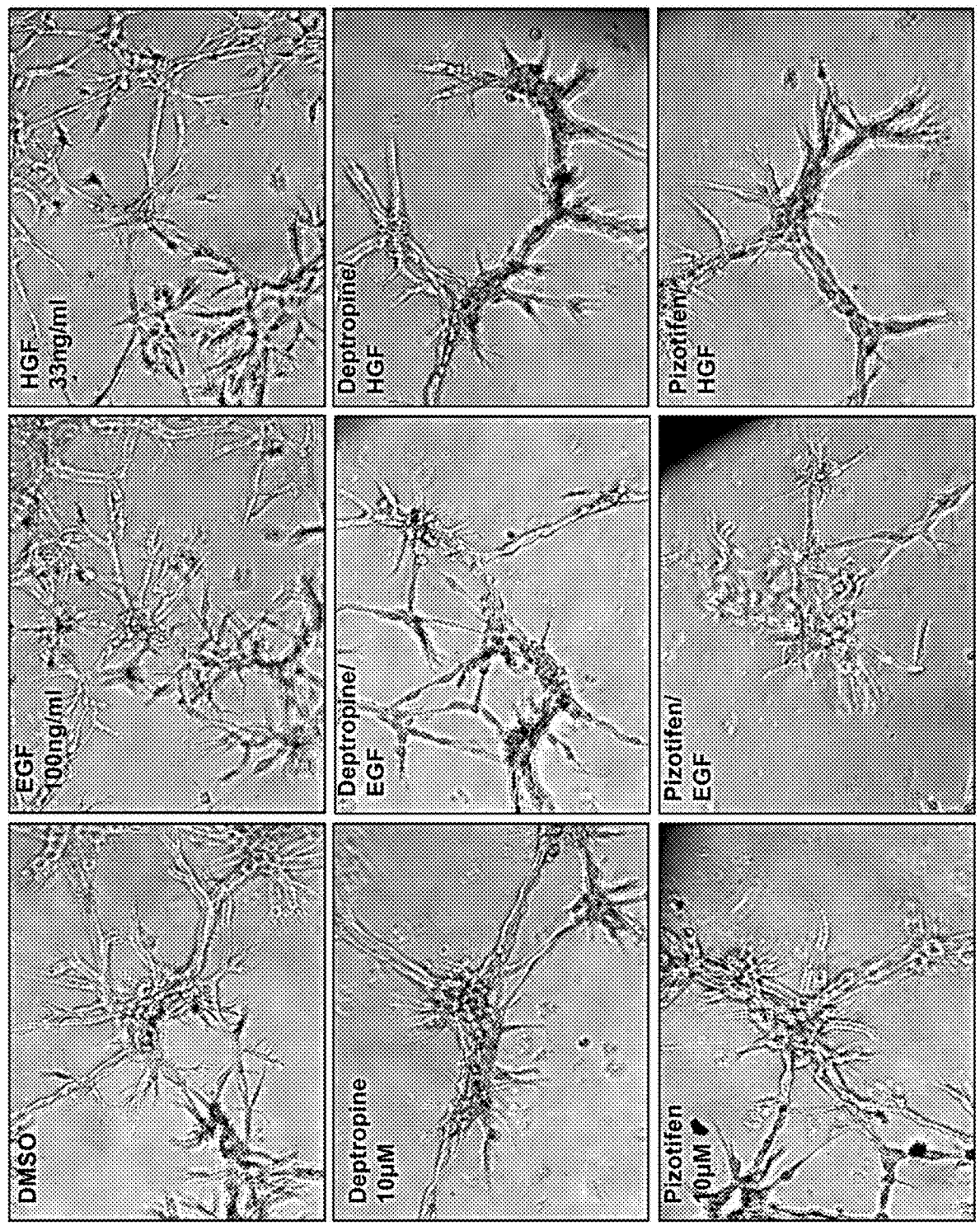
FIG. 6C is nine photographs demonstrating results of treatment with deptropine or pizotifen in A172 glioblastoma cells in 3D culture.
Figure 7:
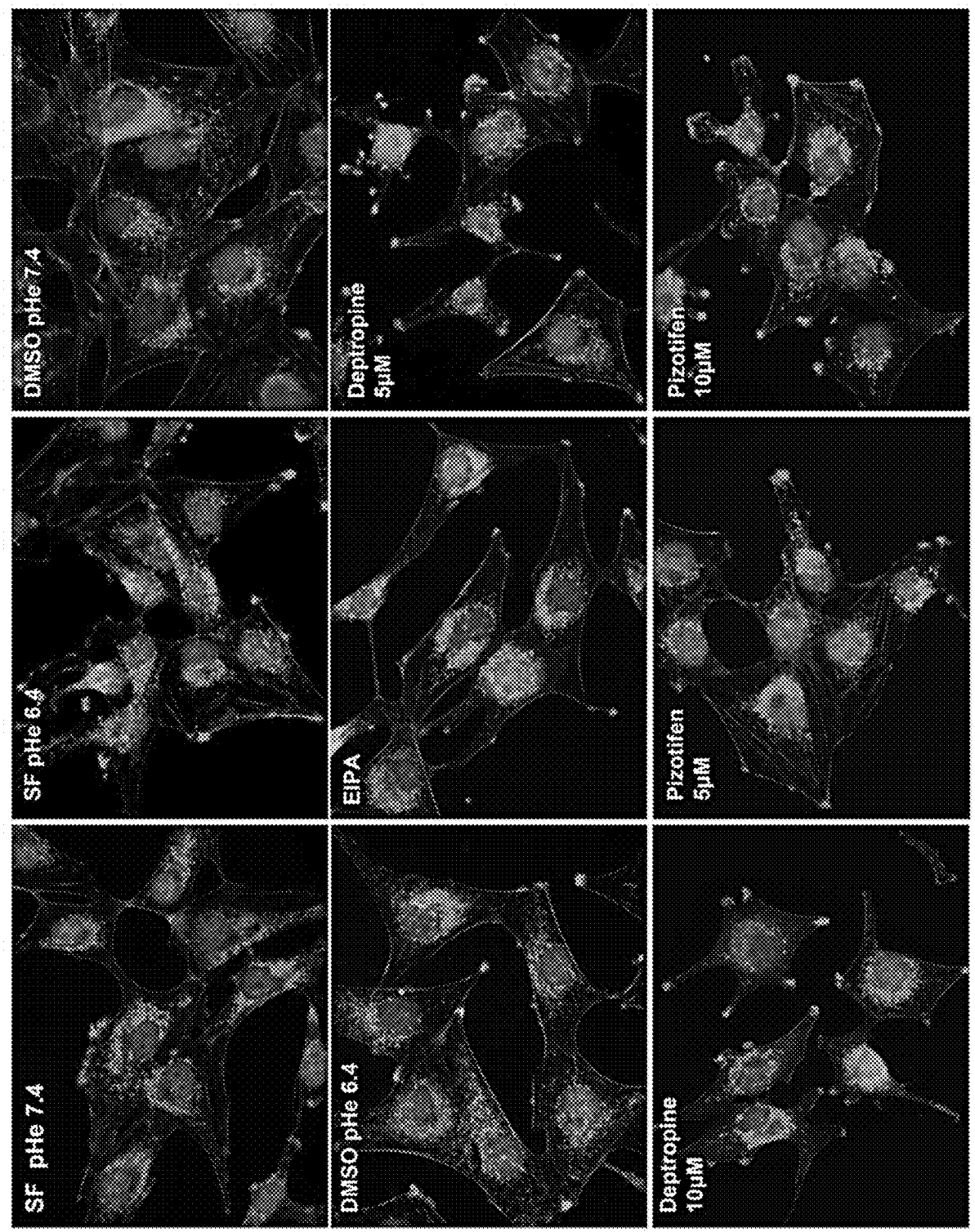
FIG. 7 is nine photographs demonstrating results after four hours of treatment with deptropine or pizotifen in A172 glioblastoma cells.

An important aspect of this technology is the showing that deptropine and pizotifen block tumor invasion using 3D assays. As shown in FIG. 6, deptropine and pizotifen decrease motility and invasion of A172 glioblastoma cells. For this experiment A172 glioblastoma cells were treated with 5 or 10 µM deptropine or pizotifen or drug mix at 5 µM concentration for 8 h prior to the wounding and the addition of matrigel. Upon wounding, cells were allowed to migrate or invade through matrigel in the presence of DMSO, 5 or 10 µM deptropine or pizotifen or the drug mix at 5 µM concentration. EIPA, a known inhibitor of lysosomal outward movement, is the positive control. Motility and invasion were calculated by Incucyte platform that acquires real time images of invasion and motility and calculate the relative wound density percentage at different time points. Percent migration (FIG. 6A) or invasion (FIG. 6B) through matrigel in A172 glioblastoma cells in the presence of DMSO, 5 or 10 µM deptropine or pizotifen or the drug mix at 5 µM concentration. Error bars represent s.e.m. of 5 separate experiments. # statistical significance, p<0.001, versus both 1% FBS and DMSO; *, p<0.01 versus both 1% FBS and DMSO FIG. 6B demonstrates that 10 µM pizotifen significantly reduces invasion of glioma cells through matrigel. In addition, 5 µM of deptropine and pizotifen significantly reduces motility (FIG. 6A) of A172 glioma cells while either drug along at 10 µM reduces motility but to a level that is determined to be significant. Finally, as shown in FIG. 6C, deptropine and pizotifen also effectively reduce the number of invasive structures formed by A172 cells in 3D culture Turning to FIG. 7, an additional aspect of this technology is how quickly deptropine and pizotifen act to move lysosomes towards the nucleus. As shown in FIG. 7: deptropine and pizotifen prevent lysosomal outward movement early as 4 hours after addition of these drugs. A172 glioblastoma cells were treated with the 5 or 10 µM deptropine or pizofifen for 2 h and then with low pHe media containing the drugs for an additional 2 hours. At the end of incubation time, cells were fixed and stained for LAMP-1, filamentous actin, and nuclei. Representative merged IF images depicting the effect of DMSO, 5 and 10 µM deptropine or pizotifen upon 4 hours on the distribution of lysosomes, colored red in color images, in A172 glioblastoma cells. Also shown in color images are actin, colored green, and nuclei, colored blue.

Figure 8:
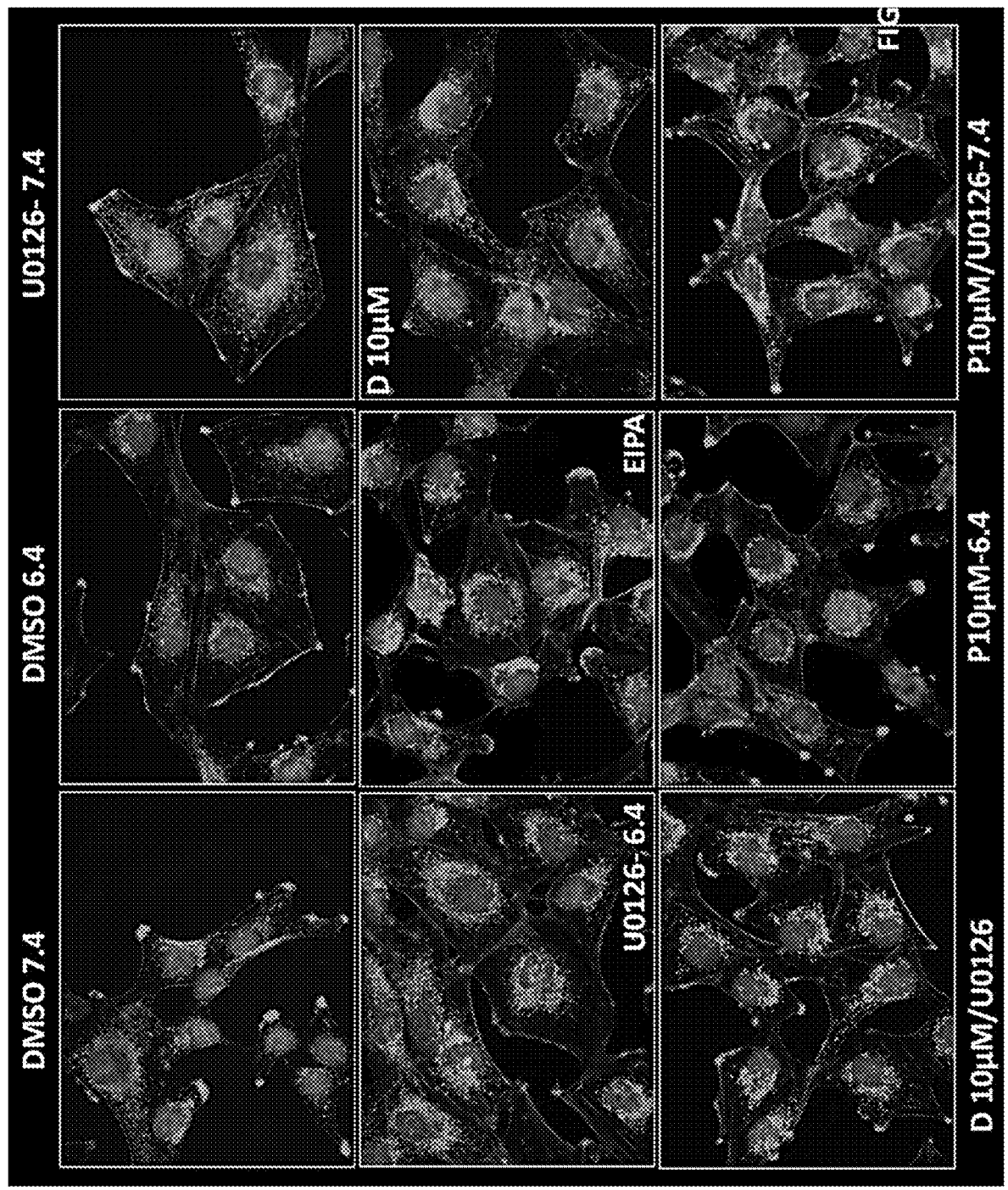
FIG. 8 is nine photographs demonstrating results of treatment with deptropine or pizotifen in A172 glioblastoma cells in the presence of U0126, a MAP-kinase inhibitor.

Turning to FIG. 8, deptropine and pizotifen are shown to act through the Erk signaling pathway. In this experiment, A172 cells were treated with deptropine and pizotifen at 5 µM concentrations for 4 hours in the presence of the MAPK inhibitor U0126. I.F. microscopy was then performed. This helped allow the determination of the mechanism of action of deptropine and pizotifen. These results demonstrate that the activity of deptropine and pizotifen to induce inward movement of lysosomes is strongly moderated by the activity of the Erk signaling pathway. The addition of U0126, a MEK inhibitor, prevents the action of deptropine and pizotifen and lysosomes remain in a more peripheral position in the tumor cells. Consistent with this observation, western blot analysis (results not shown) indicated that deptropine and pizotifen may also be used to activate the Erk signaling pathway.

Figure 9:
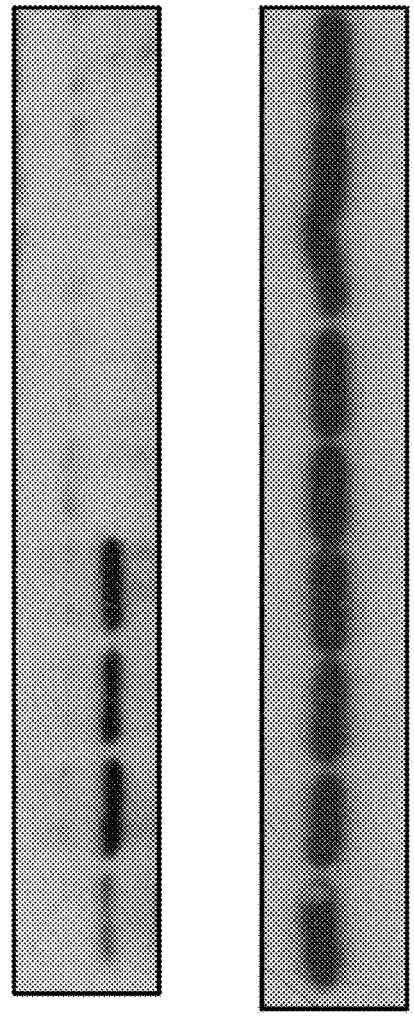
FIG. 9 is a western blot analysis of A172 glioblastoma cells after four hours of treatment with deptropine or pizotifen.

As shown in FIG. 9, embodiment aspect of this technology is that use of deptropine and pizotifen to inhibit the mTOR signaling pathway. Deptropine and pizotifen were added to A172 cells for 4 hours and western blot analysis was performed to measure levels of phosphorylated S6K, indicative of active mTOR signaling. FIG. 9 demonstrates that the addition of deptropine or pizotifen eliminates the phosphorylation of S6K, a downstream signaling component of mTOR.

Figure 10:
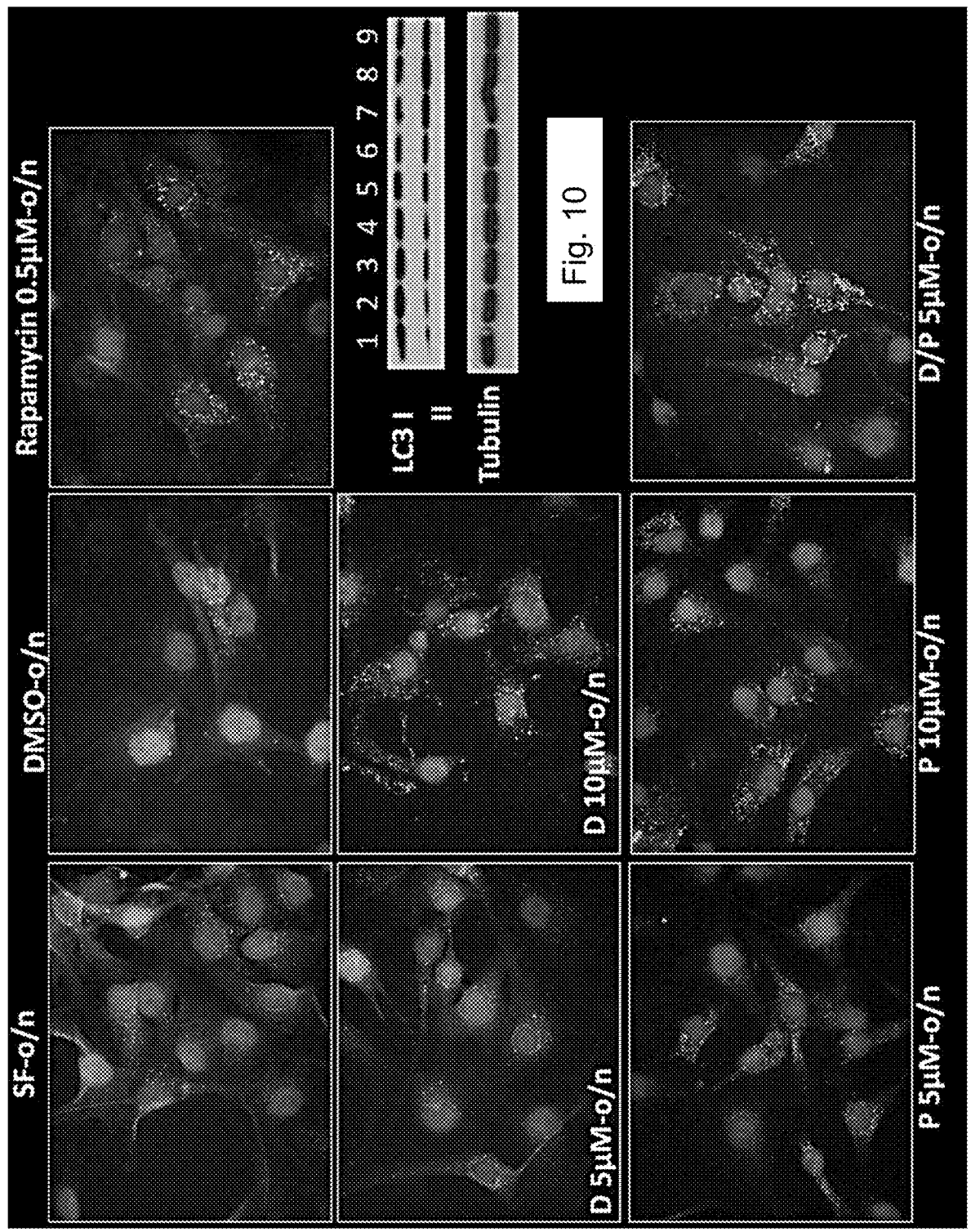
FIG. 10 is nine photographs and a western blot analysis of A172 glioblastoma cells after treatment with deptropine or pizotifen.

A further embodiment of this technology is the use of deptropine and pizotifen to induce autophagy. A172 cells were treated with EIPA (1), Serum (2), Serum Free (3), DMSO (4, solvent control), rapamycin 0.5 micromolar (5), one micromolar (6), deptropine at 5 micromolar (7), 10 micromolar (8) or pizotifen at 5 micromolar (9) overnight and GFP-LC3II was visualized by microscopy or western blot analysis was performed to detect LC3-I and LC3-II forms. The western blot analysis shown in FIG. 10 demonstrates that the addition of deptropine or pizotifen to glioma tumor cells increases the levels of the proteins LC3-II, which is cleaved upon association with forming autophagosomes. Also shown in FIG. 10 are that deptropine or pizotifen increase the association GFP-LC3-II with puncta representing autophagosomes.

Figure 11:
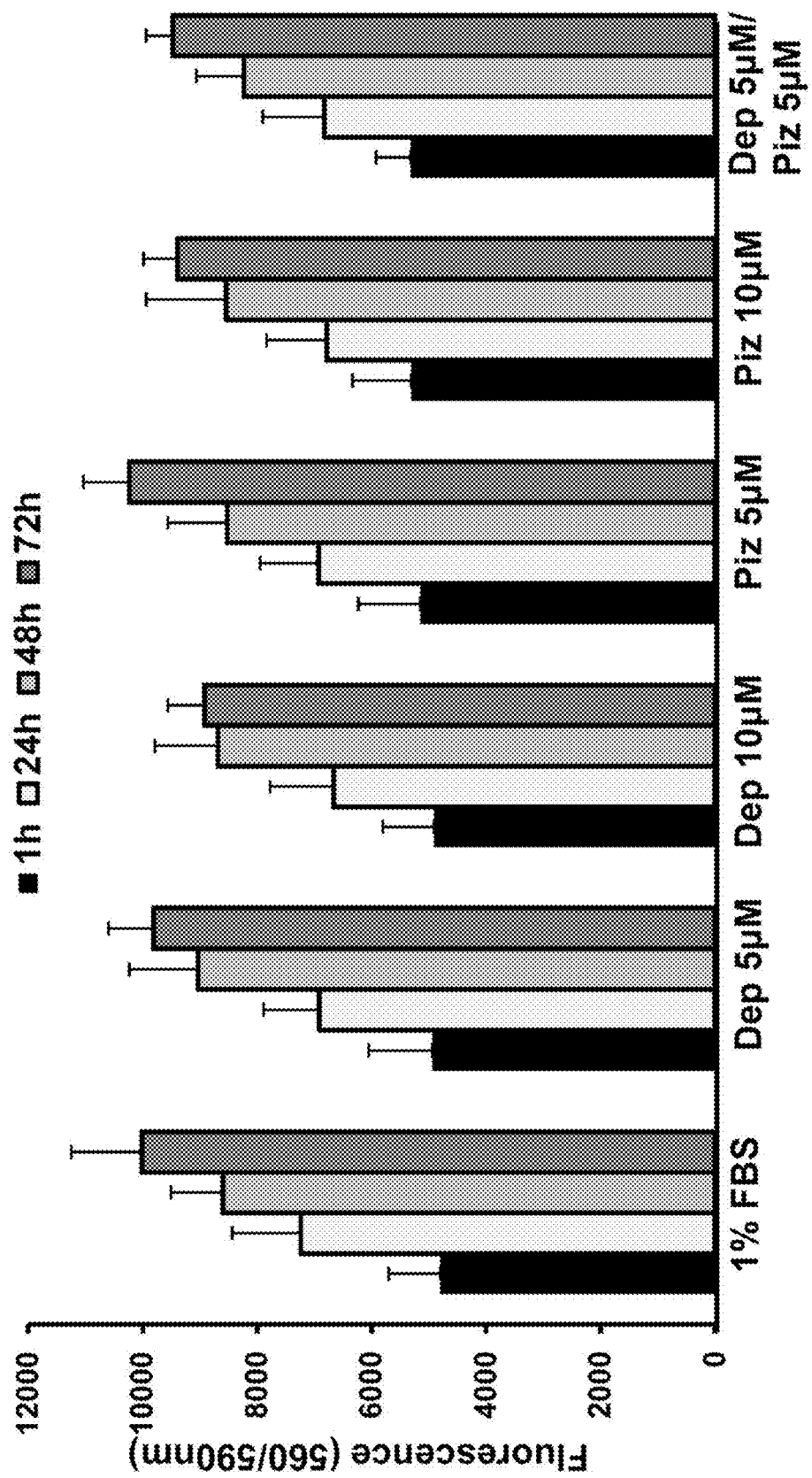
FIG. 11 is a graph showing cell proliferation after treatment with deptropine or pizotifen.

A very beneficial aspect of the treatment with deptropine and pizotifen is shown in FIG. 11, namely that the actions of deptropine and pizotifen are not the result of toxicity. The standard MTS assay was performed for A172 cells in the presence of the indicate concentrations of deptropine and pizotifen. The results in this Fig. indicate that deptropine and pizotifen at concentrations up to 10 micromolar do not inhibit proliferation of cultures of 172 tumor cells.

Treatment of cancer via deptropine and pizotifen offers many benefits in efficacy and reduced toxicity. Deptropine and pizotifen are ideally used to treat cancers, especially invasive gliomas. Chemically related compounds to deptropine and pizotifen, obvious to those of ordinary skill in the art, could also be used in treatments.

The applications of deptropine and pizotifen, in addition to the remainder of lysosome migration inhibitors alone and in combination, are numerous. In addition to gliomas, other invasive cancers can be treated with deptropine, pizotifen, or other identified lysosome migration inhibitors, or combinations thereof. Deptropine, pizotifen, or other identified lysosome migration inhibitors, can be used to treat cancer separately, or in combination(s) with each other at concentrations of 0.1 micromolar to 5 micromolar, and more preferably 0.5 micromolar to 1.5 micormolar, and most preferably at 1.0 micromolar. Other dosages for deptropine, pizotifen, or other identified lysosome migration inhibitors, or combinations thereof, to treat cancer would preferably be 0.1 to 100 mg/kg, more preferably be 1 to 20 mg/kg, and most preferably be 5 to 10 mg/kg (drug mass to animal mass) administered i.p.

Additionally, deptropine, pizotifen, or other identified lysosome migration inhibitors, or combinations thereof, may be used to treat cancer with the addition of other drugs known to prevent lysosome migration, including troglitazone, niclosamide and cambinol. This would prevent lysosome movement, and thus improve treatment, via multiple pathways. Further, deptropine, pizotifen, or other identified lysosome migration inhibitors, or combinations thereof, may be used to treat cancer in combination with other chemotherapeutic agents. This would allow multiple front approach to treating cancer. Further still, deptropine, pizotifen, or other identified lysosome migration inhibitors, or combinations thereof, may be used to treat cancer in combination with drugs that stimulate lysosome membrane permeabilization to increase efficacy.

On another front, deptropine, pizotifen, or other identified lysosome migration inhibitors, or combinations thereof, would likely be effective in non-cancer human and mammalian diseases where the position of lysosomes can influence disease progression. These conditions include but are not limited to arthritis and neurological disorders.

Also, deptropine, pizotifen, or other identified lysosome migration inhibitors, or combinations thereof, may be used as mTOR inhibitors for the treatment of multiple human and mammalian diseases. The mTOR being a signaling pathway playing a major role in multiple human diseases including cancer.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

We claim:

1. A method for treating a lysosomal movement associated cancer in an animal, in which the position of lysosomes can influence cancer progression, comprising:
   administering a pharmaceutical composition containing an effective amount of deptropine and pizotifen or pharmaceutically acceptable salts, thereof.

2. The method of claim 1 wherein the pharmaceutical composition contains a further pharmaceutically active agent.

3. The method of claim 1 wherein the a pharmaceutical composition further contains an effective amount of a lysosome migration inhibitor selected from a group of dihydroergocristine, dihydroergotoxine, mefloquine, raloxifene, niclosamide, harmine, isoquercetin, vindesine, vincristine, vinorelbine, paclitaxel, colchicine, podophyllotoxin, mebendazole, albendazole, and fenbendazole, or a pharmaceutically acceptable salt, thereof.

4. The method of claim 3 wherein the pharmaceutical composition contains an effective amount of a further lysosome migration inhibitor or a pharmaceutically acceptable salt, thereof.

5. The method of claim 2 wherein the further pharmacologically effective agent is one or more are chemotherapeutic agent.

6. The method of claim 1 wherein the wherein the pharmaceutical composition is formulated with a pharmaceutically acceptable excipient.

7. The method of claim 1 further comprising the step of inhibiting an mTOR signaling pathway.

8. The method of claim 2 wherein the further pharmacologically effective agent is one of troglitazone, niclosamide and cambinol, or a pharmaceutically acceptable salt, thereof.

9. The method of claim 2 wherein the first further pharmacologically effective agent is a chemical that stimulates lysosome membrane permeabilization to increase efficacy.

* * * * *